(12) United States Patent
da Costa et al.

(10) Patent No.: US 8,551,962 B2
(45) Date of Patent: Oct. 8, 2013

(54) HIGH DOSAGE DORAMECTIN FORMULATION

(75) Inventors: Alvimar Jose da Costa, Jaboticabal (BR); Stephen Lee Secreast, Portage, MI (US); Rodrigo Valarelli, São Paulo (BR)

(73) Assignee: Zoetis LLC, Florham Park, NJ (US)

( * ) Notice: Subject to any disclaimer, the term of this patent is extended or adjusted under 35 U.S.C. 154(b) by 60 days.

(21) Appl. No.: 13/147,600

(22) PCT Filed: Feb. 2, 2010

(86) PCT No.: PCT/IB2010/050443
§ 371 (c)(1),
(2), (4) Date: Aug. 3, 2011

(87) PCT Pub. No.: WO2010/116267
PCT Pub. Date: Oct. 14, 2010

(65) Prior Publication Data
US 2011/0294751 A1    Dec. 1, 2011

Related U.S. Application Data

(60) Provisional application No. 61/219,837, filed on Jun. 24, 2009, provisional application No. 61/152,911, filed on Feb. 16, 2009.

(51) Int. Cl.
*A61K 31/70* (2006.01)
(52) U.S. Cl.
USPC ........................................................ 514/30

(58) Field of Classification Search
USPC ........................................................ 514/30
See application file for complete search history.

(56) References Cited

U.S. PATENT DOCUMENTS

| 5,089,480 | A  | 2/1992  | Gibson et al.      |
| 6,001,822 | A  | 12/1999 | Wicks et al.       |
| 6,063,394 | A  | 5/2000  | Grosse-Bley et al. |
| 6,174,540 | B1 | 1/2001  | Williams et al.    |
| 6,617,314 | B2 | 9/2003  | Grosse-Bley et al. |
| 6,699,847 | B2 | 3/2004  | Wicks et al.       |

FOREIGN PATENT DOCUMENTS

| DE | 196 38 045 | 3/1998  |
| EP | 0 393 890  | 10/1990 |
| WO | 97/11709   | 4/1997  |
| WO | 97/46204   | 12/1997 |
| WO | 00/35445   | 6/2000  |

OTHER PUBLICATIONS

PCT International Search Report, PCT/IB2010/050443, mailed Apr. 21, 2010.
Wicks et al., "Effect of formulation on the pharmacokinetics and efficacy of doramectin", Veterinary Parasitology, 49:17-26, 1993.

*Primary Examiner* — Elli Peselev
(74) *Attorney, Agent, or Firm* — Paul M. Misiak

(57) ABSTRACT

Veterinary compositions which provide a high-dose of doramectin or a high-dose veterinary combination composition which comprises doramectin and one or more other antiparasitic agents is disclosed. The compositions provide both antiparasitic efficacy and a significantly reduced withhold time.

20 Claims, 1 Drawing Sheet

Efficacy of high-dose Doramectin and high-dose commercial Ivermectin in cattle against *D.hominis* larvae
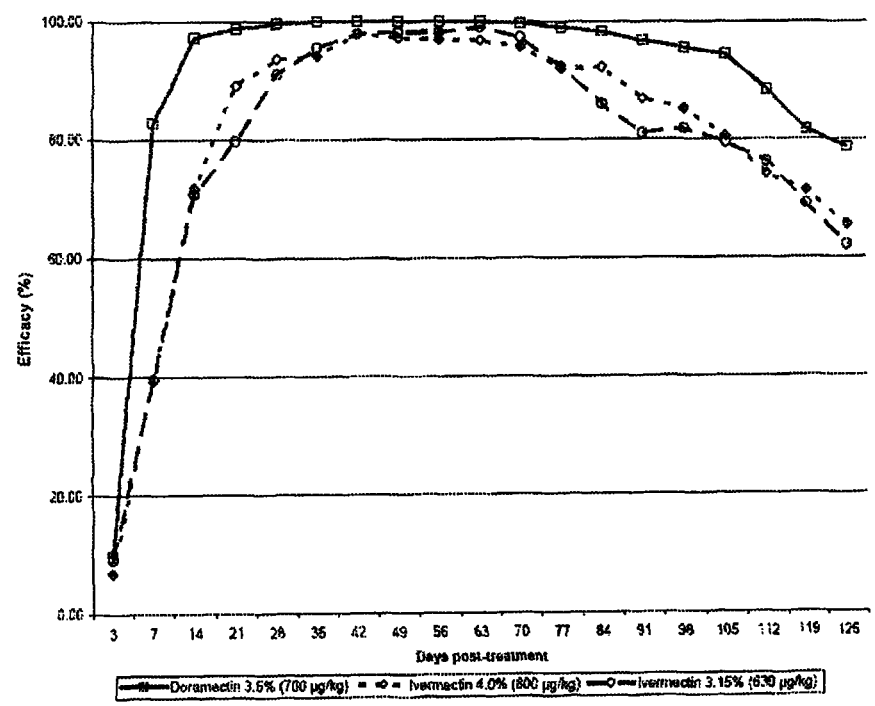

HIGH DOSAGE DORAMECTIN FORMULATION

CROSS-REFERENCE TO RELATED APPLICATIONS

This application claims priority to PCT/IB2010/050443, filed Feb. 2, 2010, which claims the benefit of U.S. Provisional Application Ser. No. 61/219,837, filed Jun. 24, 2009, and U.S. Provisional Application Ser. No. 61/152,911, filed Feb. 16, 2009. This application and all applications and prior publications either therein or cited herein (including documents cited in the text or during prosecution) are expressly incorporated by reference.

FIELD OF INVENTION

This invention relates generally to the field of antiparasitic compositions. In particular, this invention relates to a high-dose doramectin composition which is efficacious and provides a short withhold time in treated animals.

BACKGROUND OF THE INVENTION

Broad spectrum macrocyclic lactones, for example, avermectins and milbemycin, are antiparasitic agents with anthelmintic, endoparasiticide, ectoparasiticide, acaricide, and insecticide utility. Parasites which may be controlled with these broad spectrum agents include: gastrointestinal roundworms (e.g., *Ostertagia* spp., *Haemonchus* spp., *Trichostrongylus* spp., *Cooperia* spp., *Bunostomum* spp., *Strongyloides* spp., *Oesophagostomum* spp., and *Trichuris* spp.); lungworms (e.g., *Dictyocaulus viviparus*); eyeworms (e.g., *Thelazia* spp.); parasitic stage grubs (e.g., *Hypoderma* spp.), and *Dermatobia hominis*); biting and sucking lice (e.g., *Damalinia bovis, Haematopinus eurystemus, Linognathus vituli* and *Solenopotes capillatus*); ticks (e.g., *Rhipicephalus (Boophilus) microplus*); mites (e.g., *Psoroptes bovis* and *Sarcoptes scabiei*); screwworm (e.g., *Cochliomyia hominivorax*); and horn flies (e.g., *Haematobia irritans*).

U.S. Pat. Nos. 6,063,394, 6,699,847, and U.S. Pat. No. 6,617,314 relate to injectable compositions containing avermectins and/or milbemycin in triglyceride oils (sesame, castor, fractionated coconut oil), ethyl oleate; medium-chain triglycerides or glycol esters or fatty acid esters; co-solvents selected from mono- or polyhydric aliphatic or aromatic alcohols and their derivatives; and auxiliaries such as antioxidants and preservatives.

U.S. Pat. No. 6,174,540 relates to a long acting injectable composition comprising a therapeutic agent selected from the group consisting of insecticides, acaricides, parasiticides, growth enhancers, and oil soluble NSAIDS; hydrogenated castor oil; and a hydrophobic carrier comprising triacetin, benzyl benzoate, or ethyl oleate, or combinations thereof; and acylated monoglycerides, various medium chain esters, or a combination thereof.

U.S. Pat. No. 5,089,480 relates to avermectins and compositions thereof. U.S. Pat. No. 6,001,822 relates to a pharmaceutical composition comprising a solution of doramectin in a solvent consisting of sesame oil and ethyl oleate. An injectable doramectin composition containing 1% (w/v) doramectin (10 mg/mL) in a combination of sesame oil and ethyl oleate is sold by Pfizer under the trade name Dectomax® for the treatment of parasitic infections in cattle.

Following treatment, residual macrocyclic lactones can be found in animal tissue for extended periods of time. Thus, when an animal is treated with a macrocyclic lactone there is a withhold time in which the animal cannot be slaughtered for human consumption. Specifically, when beef cattle are given a single dose of doramectin at the recommended dose of 200 μg/Kg of body weight, which is equivalent to 10 mg/110 pounds of body weight, the withhold time is 35 days.

Further, it is known that numerous parasites can and have become resistant to many of the current commercial antiparasitic products. In an effort to combat resistance, higher doses of the antiparasitic agents have been formulated. As described above, averemectins and milbemycin have been formulated with castor oil and ethyl oleate because of their increased solubility. Subsequently, high solubility equates to a high oil affinity which affects the release rate of the drug from the oil. As drug concentration increases, there is a slower release rate which is associated with a longer withhold time. In some instances, high doses of avermectin and milbemycin will precipitate out of solution as a result of a low partition coefficient between oil and drug. If this occurs, residual drug concentrations at the injection site can be high. Thus, absorption and release rate is slow and withhold time is extended. Therefore, cattle dosed with higher concentrations of avermectins and/or milbemycin can not be timely slaughtered thereby increasing herd management costs and subsequently consumer cost. The compositions of the present invention provide a high dose of an avermectin and/or milbemycin, preferably doramectin, that provides increased efficacy against parasites with a substantially shorter withhold time.

All of the above recited U.S. patents and publications are incorporated herein by reference.

SUMMARY OF THE INVENTION

This invention relates to a veterinarily acceptable antiparasitic high-dose doramectin composition further comprising a long chain trigyleride, a co-solvent, and optionally, one or more each of a preservative and auxiliary excipient.

In another aspect of the invention, the composition comprises (a) 3-6% by weight doramectin; (b) 39-60% by volume cottonseed oil; (c) 30-50% by volume benzyl benzoate; and optionally one or more each of a preservative and auxiliary excipient.

In another aspect of the invention, the composition comprises 3-6% by weight doramectin. Preferably, the doramectin is 3-4% by weight. More preferably, the doramectin is 3.5% by weight.

In another aspect of the invention, the composition comprises 39-60% by volume cotton seed oil. Preferably, 50-60% by volume cotton seed oil and more preferably, 55% by volume cotton seed oil.

In another aspect of the invention, the composition comprises 30-50% by volume benzyl benzoate. Preferably, the benzyl benzoate is 35-45% by volume and more preferably 39% by volume.

In another aspect of the invention, the composition comprises at least one preservative. Preferably, the preservative is tocopherol. More preferably, the preservative is tocopherol acetate.

In another aspect of the invention, the composition comprises at least one auxiliary excipient. Preferably, the auxiliary excipient is benzyl alcohol.

In another aspect of the invention, the composition comprises at least one each of a preservative and an auxiliary excipient. The preferred and more preferred preservative and preferred auxiliary excipient is as defined above.

In another aspect of the invention, the composition comprises 3.5% by weight doramectin, 55% by volume cottonseed oil, 39% by volume benzyl benzoate, 6% by volume benzyl alcohol, and 0.05% by weight tocopherol acetate.

In another aspect of the invention, is a method for the prevention, treatment, or control of parasites in animals which comprises administering to said animal in need thereof, an effective amount of the high-dose doramectin veterinary composition. The preferred animal is livestock. The most preferred animal is cattle.

In another aspect of the invention, is a method of parenterally administering the high-dose doramectin antiparasitic composition. Preferably, the composition is administered intramuscularly or subcutaneously. More preferred, the high-dose doramectin antiparasitic composition is administered subcutaneously.

In another aspect of the invention, is a combination veterinary composition comprising a) doramectin, b) one or more other antiparasitic agents, c) cotton seed oil, d) benzyl benzoate, and optionally, e) one or more each of a preservative and auxiliary excipient. Preferably, the doramectin is about 1-3% by weight and the other antiparasitic agents, alone or combined, are about 1-3% by weight.

In another aspect of the invention, is a combination veterinary composition where the preferred other antiparasitic agent is selected from ivermectin, abamectin, eprinomectin, and moxidectin.

In another aspect of the invention, is a combination veterinary composition, comprising doramectin and abamectin, doramectin and eprinomectin, doramectin and ivermectin, and doramectin and moxidectin.

In another aspect of the invention, is a combination veterinary composition comprising doramectin and two other antiparasitic agents selected from abamectin, eprinomectin, ivermectin and moxidectin (e.g., doramectin, abamectin, and ivermectin; doramectin, ivermectin, and eprinomectin; doramectin, ivermectin and moxidectin; and the like).

In another aspect of the invention, is a combination veterinary composition comprising a) 1-3% by weight doramectin, b)1-3% by weight of one other antiparasitic agent or 1-3% combined weight of more than one other antiparasitic agent, c) 39-75% by volume cotton seed oil, d) 25-50% by volume benzyl benzoate, and optionally, e) one or more each of a preservative and auxiliary agent. The preferred and most preferred other antiparasitic agents, preservatives, and auxiliary agents are as defined herein.

In another aspect of the invention, is a method for the prevention, treatment, or control of parasites in animals which comprises administering to said animal in need thereof, an effective amount of the combination veterinary composition. The preferred animal is livestock. The most preferred animal is cattle.

In another aspect of the invention, is a method of parenterally administering the combination composition. Preferably, the combination composition is administered intramuscularly or subcutaneously. More preferred, the high-dose combination composition is administered subcutaneously.

In another aspect of the invention, the veterinary composition or veterinary combination composition, as described above, further comprises at least one or more fat-soluble vitamins. The preferred fat soluble vitamins are Vitamins A, D, and E. The preferred preservatives for the vitamin enriched compositions are phenol, m-cresol, BHA and BHT. The more preferred preservatives are BHA and BHT.

In another aspect of the invention, is a method for the prevention, treatment, or control of parasites in animals which comprises administering to said animal in need thereof, an effective amount of the veterinary composition or veterinary combination composition with a fat-soluble vitamin(s). The preferred animal is livestock, the most preferred animal is cattle.

In another aspect of the invention, is a method of parenterally administering the veterinary composition or veterinary combination composition with at least one or more fat-soluble vitamins. Preferably, the compositions are administered intramuscularly or subcutaneously. More preferred, the compositions are administered subcutaneously.

DETAILED DESCRIPTION

The present invention provides a high-dose doramectin composition that is useful as an efficacious antiparasitic agent and provides reduced withhold times in animals following administration.

DRAWINGS

FIG. 1 depicts the efficacy of single high-dose doramectin and high-dose ivermectin in cattle against D.hominis larvae.

DEFINITIONS

For purposes of the present invention, as described and claimed herein, the following terms and phrases are defined as follows:

"Animal", as used herein, unless otherwise indicated, refers to an individual animal that is a member of the taxonomic class Mammalia. Non-exclusive examples of animals include dogs, cats, horses, swine, sheep, goats, and cattle.

"Parasite" or "parasites", as used herein, unless otherwise indicated, refers to endoparasites and ectoparasites including acarids, insects, helminthes, and their respective larvae, pupae, grubs, nymphs, and the like "Parenteral", as used herein, unless otherwise indicated, refers to a form of administration which is intramuscular (e.g., into a muscle), subcutaneous (e.g., under the skin), intradermal (e.g., into the skin itself), and intravenous (e.g., into a vein).

"Preservative(s)", as used herein, unless otherwise indicated, refers to a substance or substances which are added to the compositions of the present invention to protect them from microbial action and chemical reaction. The term includes antioxidants (free radical scavengers) which protect the compositions from chemical reactions by scavenging free radicals thereby eliminating electron transfer from one compound or substance to another.

"Treatment", "treating", and the like, as used herein, unless otherwise indicated, refers to reversing, alleviating, or preventing the disorder or condition to which such term applies. Thus, treatment can refer to administration of the composition of the present invention to an animal that is not at the time of administration afflicted with the disorder or condition.

"Veterinarily acceptable"—as used herein, unless otherwise indicated, indicates that the substance or composition must be compatible chemically and/or toxicologically, with the other ingredients comprising a composition, and/or the animal being treated therewith.

"Withhold time", as used herein, unless otherwise indicated, refers to the period of time (e.g., days) after the last dose of drug administration during which time an animal cannot be slaughtered for human consumption.

DESCRIPTION

This invention relates to a high-dose doramectin composition comprising 3-6% (w/v) doramectin, 39-60% (v/v) cottonseed oil, and 30-50% (v/v) benzyl benzoate. Optionally, the composition may contain one or more auxiliary excipients including antioxidants, preservatives and co-solvents. A typical composition is prepared by mixing an amount of doramectin with cotton seed oil, benzyl benzoate, tocopherol acetate as an antioxidant and benzyl alcohol as a co-solvent. Other common suitable antiparasitic agents, veterinarily acceptable vegetable or synthetic oils and esters, co-solvents, antioxidants, and preservatives recognized by persons skilled in the art as safe for administration to an animal can be used. However, development of a parenteral composition utilizing an avermectin and/or milbemycin requires an understanding of the interaction between the drug and the other carriers and excipients of the composition. The avermectin and milbemycin antiparasitic agents are highly soluble in castor oil, however, because of the binding affinity between the agent and the oil, the agent is not readily released from the oil. Therefore, residual concentrations of the agent remain high at the site of injection. Secondly, the avermectins have lower solubility profiles in other oils (e.g., ethyl oleate, fractionated coconut oil, sesame oil, and cotton seed oil). The lower solubility does not allow for high-dose compositions. Therefore, other co-solvents are needed to ensure high-dose solubility while maintaining low binding affinities. Finally, depending upon the aqueous nature of the composition, the high-dose avermectins can precipitate as a result of the agent partitioning to the aqueous phase.

The active antiparasitic agent which is particularly emphasized in the present invention is doramectin (3-6%) by weight. Preferably, doramectin is 3-4% by weight, and more preferably 3.5% by weight.

Suitable vegetable oils include long-chain triglycerides, for example, cotton seed oil, sesame oil, soybean oil, corn oil, and the like. The $C_8/C_{10}$ medium chain triglyercides (e.g., Miglyol 810 or 812) can also be used.

Suitable co-solvents include esters, for example, benzyl benzoate, ethyl oleate, tributyl citrate, tributylacetyl citrate, and $C_8/C_{10}$ medium chain propylene glycol diesters (e.g., Miglyol 840). Benzyl benzoate is preferred as it is unique among the esters since it provides good doramectin solubility with moderate binding affinity, unlike castor oil, a long-chain triglyceride. Additionally, because of the moderate affinity, the injection site clearance rate for doramectin is quicker. Therefore, the cotton seed oil and benzyl benzoate composition allow doramectin to remain solubilized while managing injection site absorption, clearance, and ultimately reduced withhold time.

Auxiliary excipients can also be used in the composition. These co-solvents are generally added to the composition in volumes ranging from about 2 to 8%. Suitable auxiliary excipients include benzyl alcohol, propylene glycol or other non-toxic polyhydroxy alcohols, including, for example, polyethylene glycol. Benzyl alcohol is useful as a mild anesthetic for parenteral compositions thereby reducing injection site pain and subsequently promoting injection site toleration.

Preservatives can also be used to ensure the overall stability of the composition. Depending upon whether the compositional preservative is added to control or prevent antimicrobial growth and/or as an antioxidant to control or prevent chemical reactions, the amounts of each preservative can range from about 0.01% to about 2% by weight and/or volume of the composition. For example, tocopherol acetate can be added at a range from about 0.01% to about 0.10% by weight; BHA and BHT can each be added to a single composition at a range each from about 0.05 to 0.5%. Non-limiting suitable preservatives include: phenylethanol, phenol, m-cresol, benzalkonium, parabens, butylhydroxyanisole (BHA), butylhydroxy toluene (BHT), propyl gallate, and the like. Some non-limiting preservatives which are antioxidants include: Vitamin A, carotenoids, ascorbates, flavonoids, polyphenols, isothiocyanates, lycopene, cysteine, tocopherols (which include $\alpha$, $\beta$, $\gamma$, $\delta$ tocopherols, mixtures thereof, and the esters of tocopherol (e.g., acetate and succinate)), and the like.

The composition of the present invention may also include an amount of at least one or more fat-soluble vitamins. The preferred fat soluble vitamins are Vitamin A, Vitamin D, and Vitamin E. The recommended vitamin requirements in cattle range from about 2000 to 4000 IU/kg (Vitamin A), about 275 IU/kg (Vitamin D), and 15 to 60 IU/kg (Vitmain E). Since these fat soluble vitamins are primarily stored in liver and adipose tissues, higher doses can be administered. The stored vitamins are slowly excreted over time thereby providing extended vitamin nutrition. Single bolus doses of Vitamin A, D, and E can range from about 100,000 to 500,000 IU/mL, 10,000 to 75,000 IU/mL, and about 5 to 300 IU/mL, respectively. Depending upon the age of the animal, doses can be administered to provide about 2000 to 5000 IU/kg for Vitamin A, about 200 to 600 IU/kg for Vitamin D, and about 0.5 to 7 IU/kg for Vitamin E. Over time, these doses provide a daily amount of vitamin A ranging from about 50 to 125 IU/kg/day for 40 days and about 33-83 IU/kg/day for 60 days; about 5 to 22 IU/kg/day for 40 days and about 3 to 15 IU/kg/day for 60 days for Vitamin D; and about 0.02 to 0.15 IU/kg/day for 40 days and about 0.01 to 0.10 IU/kg/day for 60 days for Vitamin E.

The compositions of the present invention can be prepared using conventional dissolution and mixing procedures to prepare a veterinary dosage form to provide an easily controllable dosage of the drug and an easily handled product.

The composition (Example 1) of the present invention was prepared using typical manufacturing operations for injectable solutions. Doramectin was solubilized in benzyl benzoate at about 55° C. Tocopherol acetate was separately solubilized in benzyl benzoate and then added to the doramectin solution. Benzyl alcohol and cotton seed oil were solubilized by adding the excipients to the doramectin solution. The doramectin solution was mixed at about 55° C. for about 1-2 hours without nitrogen sparging or vacuum. The solution was then sparged with nitrogen under vacuum. The solution was cooled to about 25° C. and then filtered with a 1 micron pre-filter and a 0.22 micron sterilizing filter. The filtered solution was then deposited to sterile amber glass vials and capped.

Compositions within the scope of the invention have been shown to provide efficacy against economically important endoparasites and ectoparasites following a single injection with a significantly reduced withhold time. This represents a significant advantage for those working in the field of livestock animals as it offers effective high-dose treatment with reduced withhold time. If the withhold time can be significantly reduced, while effectively treating the animal for endo and ectoparasites, then the animal, preferably cattle, can be slaughtered for human consumption at a much sooner time following dose administration. Subsequently, the cost to the cattle rancher, feed lot manager or other entity, and ultimately the consumer, will be greatly reduced. Additionally, if the animal can be slaughtered sooner, there is a reduced risk of re-infection, particularly in animals with residual drug concentrations which prevent slaughter as a result of the extended withhold time but are to low to be efficacious.

Among the parasites (adult and larval) which may be controlled with the high-dose composition of the present invention are roundworms, lungworms, eyeworms, kidneyworms, grubs, sucking and biting lice, ticks, and mange mites. The gastrointestinal roundworms include, for example, *Ostertagia ostertagi* (including inhibited larvae), *O. lyrata, Haemonchus placei, H. similis, H. contortus, Trichostrongylus axei, T. colubriformis, T. longispicularis, Cooperia oncophora, C. pectinata, C. punctata, C. surnabada* (syn. *mcmasteri*), *C. spatula, Ascaris suum, Hyostrongylus rubidus, Bunostomum phlebotomum, Capillaria bovis, B. trigonocephalum, Strongyloides papillosus, S. ransomi, Oesophagostomum radiatum, O. dentatum, O. columbianum, O. quadrispinulatum, Trichuris* spp., and the like. Other parasites include lungworms (e.g., *Dictyocaulus viviparus* and *Metastrongylus* spp); eyeworms (e.g., *Thelazia* spp.); parasitic stage grubs (e.g., *Hypoderma bovis, H. lineatum, Dermatobia hominis*); kidneyworms (e.g., *Stephanurus dentatus*); sucking and biting lice (e.g., *Haematopinus eurysternus, H. suis, Linognathus vituli, Solenopotes capillatus, Damalinia bovis*); screw worm (e.g., *Cochliomyia hominivorax* (larvae); ticks (*Rhipicephalus Boophilus microplus, R. sanguineus,*), *I. ricinus, I. hexagonus, Dermacentor variabilis, D. andersoni, D. marginatus, Amblyomma maculatum, A. triste, A. parvum, A. cajennense, A. ovale, A. oblongoguttatum, A. aureolatum, A. cajennense,* and the like); mange mites (e.g., *Psoroptes bovis, Sarcoptes scabiei*); and horn flies (e.g., *Haematobia irritans*).

The compositions of the invention can be administered in a way appropriate to the specific use envisaged, the particular host animal and weight of host animal being treated, the parasite or parasites involved, degree of infestation, etc., according to standard veterinary practice. Preferably, the compositions of the present invention are formulated for parenteral administration. More preferably, the composition is formulated for intramuscular and subcutaneous injection. Injection of the composition can be accomplished using a suitable veterinary dosing device, such as a syringe or an injection gun of the types available from such suppliers as NJ Phillips Injector, Instrument Supplies and Simcrotec. Choice of the injection device depends on a number of factors such as the viscosity of the composition, capability to deliver a unit dose of active drug in field conditions, etc., and according to standard veterinary practice.

The veterinary practitioner, or one skilled in the art, will be able to determine the dosage suitable for the particular animal, which may vary with the species, age, weight, and response. The average doses are exemplary of the average case. Accordingly, higher or lower dosage ranges may be warranted, depending upon the above factors, and are within the scope of this invention.

The composition of the present invention may be administered alone, as described above, or in combination with one or more other antiparasitic agents for a combined drug composition of 2-6% to form a multi-component pesticide giving an even broader spectrum of veterinary utility. Thus, the present invention also envisions a combination veterinary composition comprising an effective amount of doramectin and at least one additional antiparasitic agent, a long-chain triglyceride, co-solvent, and optionally, one or more each of a preservative and auxiliary excipient, as defined above. Specific further antiparasitic agents include ivermectin, eprinomectin, abamectin, moxidectin, and milbemycin. For simultaneous administration, doramectin and the other antiparasitic agent(s) can be combined into a single pharmaceutical composition. For example, the composition can be formulated in cotton seed oil and benzyl benzoate with from 1-3% doramectin in combination with 1-3% of one other antiparasitic agent, or 1-3% doramectin in combination with at least two other antiparasitic agents with a combined weight of about 1-3%, optionally with one or more each of a preservative and auxiliary excipient. Non-exclusive combination compositions include: 1% doramectin and 1% abamectin; 1.5% doramectin, 1% abamectin and 1% ivermectin; 1% doramectin, 1% abamectin, and 2% ivermectin, and the like. The combination veterinary compositions can be formulated according to the methods described above.

Inasmuch as it may be desirable to administer a combination of active compounds in a single composition, for example, for the purpose of treating a particular disease or condition, it is within the scope of the present invention that two or more veterinary compositions, at least one of which contains doramectin, in accordance with the invention, may conveniently be combined in the form of a kit suitable for co-administration of the compositions.

Thus, this invention also relates to a kit comprising two or more separate veterinary compositions, at least one of which contains doramectin in accordance with the invention, and means for separately retaining said compositions, such as a container, divided bottle, sachets, ampoule, or divided foil packet. To assist compliance, the kit typically comprises directions for administration and may be provided with a so-called memory aid.

The veterinary composition for application may be packaged in a variety of ways depending upon the method used for administering the drug. Generally, an article for distribution includes a container having deposited therein the veterinary composition in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compositions of the present invention are tolerable when used in cattle. Further, the composition of the present invention is stable at accelerated temperature and relative humidity (40° C./75%) through 6-months.

GENERAL EXPERIMENTAL PROCEDURES

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

Example 1

A composition containing 3.5% (w/v) doramectin (0.7 mg/kg), formulated in cottonseed oil, benzyl benzoate, and benzyl alcohol as set forth below was prepared.

| | |
|---|---|
| Doramectin | 3.5 g |
| Benzyl alcohol | 6.0 mL |
| Tocopheryl acetate | 0.050 g |
| Cottonseed oil | 55.0 mL |
| Benzyl benzoate q.s.p. | 100.0 mL |

Example 2

Comparative Composition

A composition containing 3.0% (w/v) doramectin (0.6 mg/kg), in a carrier comprising 40% (v/v) castor oil and 60% (v/v) ethyl oleate was prepared.

Example 3

A composition without an auxiliary excipient or preservative containing 3.5% (w/v) doramectin (0.7 mg/kg) formulated in a cottonseed oil and benzyl benzoate can be prepared as set forth below.

| | |
|---|---|
| Doramectin | 3.5 g |
| Cottonseed oil | 55.0 mL |
| Benzyl benzoate q.s.p. | 100.0 mL |

Example 4

A combination composition containing 1% (w/v) doramectin (0.2 mg/kg), 1% ivermectin (0.2 mg/kg) formulated in cottonseed oil, benzyl benzoate, benzyl alcohol, and preservative can be prepared as set forth below. A similar composition can be prepared without the preservative and/or the auxiliary excipient (benzyl alcohol).

| | |
|---|---|
| Doramectin | 1.0 g |
| Ivermectin | 1.0 g |
| Benzyl alcohol | 6.0 mL |
| Cottonseed oil | 55.0 mL |
| Tocopheryl acetate | 0.050 g |
| Benzyl benzoate q.s.p. | 100.0 mL |

Example 5

A combination composition containing 1% (w/v) doramectin (0.2 mg/kg), 1% ivermectin (0.2 mg/kg), and 1% abamectin (0.2 mg/kg) formulated in cottonseed oil, benzyl benzoate, benzyl alcohol, and tocopherol acetate can be prepared as set forth below. A similar composition can be prepared without the tocopherol and/or benzyl alcohol.

| | |
|---|---|
| Doramectin | 1.0 g |
| Ivermectin | 1.0 g |
| Abamectin | 1.0 g |
| Benzyl alcohol | 6.0 mL |
| Cottonseed oil | 55.0 mL |
| Tocopheryl acetate | 0.050 g |
| Benzyl benzoate q.s.p. | 100.0 mL |

Example 6

A composition containing 1% (w/v) doramectin (0.2 mg/kg), 1% (w/v) abamectin (0.2 mg/kg) formulated in cottonseed oil, benzyl benzoate, benzyl alcohol, Vitamin A, D, and E, and with the preservatives BHA and BHT as set out below can be prepared. The amounts of each vitamin (A, D, and/or E) can be increased or decreased accordingly to provide a certain dose (e.g., IU/kg) of vitamin(s) depending on animal age, health, and duration of supplementation required.

| Agent/Excipient | | IU/ml |
|---|---|---|
| Doramectin | 1.0 g | na |
| Abamectin | 1.0 g | na |
| retinyl palmitate (A) | 8.8 g | 160000 |
| Cholecalciferol (D) | 0.1125 g | 45000 |
| dl-alpha-tocopherol acetate (E) | 4.5 g | 45 |
| BHA | 0.2 g | na |
| BHT | 0.2 g | na |
| benzyl benzoate q.s.p. | 25 mL | na |
| cottonseed oil | qs 100 mL | na |

Oil/Water Partitioning

A number of triglyceride oil:ester solution compositions comprising doramectin alone and doramectin with other avermectins were prepared to assess the composition:water partition coefficients and extent of drug precipitation as a means of determining drug residual time. For example, if the drug/oil affinity is strong, then the drug is not readily released from the oil and if drug precipitates, then systemic absorption and clearance is even slower. Slower rates of clearance equate to longer withhold times. Triglyceride oil:ester composition vehicles were prepared at a 55:45 oil:ester v/v ratio. Solid antiparasitic agents were added to the vehicles, and dissolved by heating the solutions while mixing. Once cooled to room temperature, 1 mL of each composition was added to 10 mL water, and the mixtures equilibrated by gentle rotational mixing for 72 hours at room temperature. The oil and aqueous phases were separated by centrifugation, and the aqueous phases were further clarified by filtration if needed, to remove precipitated drug. For each composition, both phases and the initial compositions were assayed by HPLC. Results are shown below in Table 1.

TABLE 1

Antiparasitic agent triglyceride oil:ester composition - water equilibrium partition coefficients and % precipitate

| Avermectin | log $P_{FW}$[1] | % remaining in solution[2] |
|---|---|---|
| cottonseed oil:benzyl benzoate (55:45) v/v | | |
| doramectin 3.5% | 4.7 | 94% |
| abamectin 3.5% | 4.5 | 100% |
| doramectin 1% + abamectin 1% | 5.0, 4.7 | 100%, 100% |
| ivermectin 3.5% | 5.2 | 100% |
| doramectin 1% + abamectin 1% + ivermectin 1.5% | 5.0, 4.7, 5.0 | 100%, 100%, 100% |
| sesame oil:benzyl benzoate (55:45) v/v | | |
| doramectin 3.5% | 4.6 | 87% |
| abamectin 3.5% | 4.6 | 100% |
| castor oil:benzyl benzoate (55:45) v/v | | |
| doramectin 3.5% | 5.6 | 98% |
| abamectin 3.5% | 5.2 | 100% |
| cottonseed oil:ethyl oleate (55:45) v/v | | |
| doramectin 3.5% | 2.9 | 6% |
| abamectin 3.5% | 3.8 | 30% |

[1] log $P_{FW}$ = calculated composition-water partition coefficient = log ([mg/mL dissolved in oil phase]/[mg/mL dissolved in aqueous phase])
[2] % remaining in solution = ([mg dissolved in oil phase] + [mg dissolved in aqueous phase])/mg in original composition * 100

Overall, the cotton seed oil/benzyl benzoate composition provided acceptable high dose solubility and composition: water log P values for doramectin and the other avermectins, alone and in combination. Further, the composition showed good ability to maintain drug solubility upon exposure to an aqueous environment (e.g., ≥94% remained in solution), indicating a low propensity for injection site precipitation and thus reduced withhold times while providing a higher efficacious dose. Similarly, the castor oil composition showed acceptable solubility, as anticipated, however there was a significant increase in log P due to the strong affinity between the drug and oil. This affinity is expected to result in significantly prolonged injection site drug clearance. The cottonseed oil:ethyl oleate composition also showed good solubility, however, a slight decrease in water exposure tolerability results in slight increase in drug precipitation.

Biological Studies

Study 1

Forty five cattle (15/group) were castrated and the castration wounds were naturally exposed to screwworm (*Cochliomyia hominivorax* larvae) infestation. The control group received no treatment. The first treatment group received a single injected dose of the comparative composition (Example 2) at a dosage of 0.6 mg/kg. The second treatment group received a single injected dose of the composition of Example 1 at a dosage of 0.7 mg/kg. The efficacy against screw worms was calculated on Days 3 through 20 post treatment, for each treated group, on each designated day of assessment, as follows:

$$\text{Efficacy (\%)} = \frac{\text{number of actives myiasis in the control group} - \text{number of actives myiasis in the treated group}}{\text{number of actives myiasis in the control group}} \times 100$$

The results of Study 1 are shown in Table 2.

TABLE 2

Efficacy (%) of high-dose doramectin compositions against *C. hominivorax* larvae, days post treatment (DPT)

| DPT | Efficacy (%) Example 1 | Efficacy (%) Comparative Composition Example 2 |
|---|---|---|
| 3 | 100.0 | 100.0 |
| 4 | 100.0 | 25.0 |
| 5 | 100.0 | 66.7 |
| 6 | 90.0 | 80.0 |
| 7 | 90.0 | 80.0 |
| 8 | 90.9 | 100.0 |
| 9 | 100.0 | 100.0 |
| 10 | 100.0 | 100.0 |
| 11 | 100.0 | 100.0 |
| 12 | 100.0 | 100.0 |
| 13 | 100.0 | 100.0 |
| 14 | 100.0 | 100.0 |
| 16 | 85.7 | 100.0 |
| 18 | 85.7 | 100.0 |
| 20 | 100.0 | 100.0 |

Overall, the data shows an earlier onset of efficacy of the composition of the present invention (Example 1) against *C. hominivorax larvae.*

Study 2

Twenty-four naturally infected bovines with egg per gram of feces (EPG) counts superior to 500 were randomly assigned to three treatment groups based on the mean of three EPG counts (Days −3, −2 and −1). The control group received no treatment. The second group was treated with a single dose of the comparative composition (Example 2) at a dosage of 0.6 mg/kg. The third group was treated with a single dose of the composition of Example 1 at a dosage of 0.7 mg/kg. Bovines were kept in individual stalls until Day 14 post-treatment, date in which animals were euthanized and necropsied for the assessment of helminthes burden. Helminthes of several species (*Haemonchus* (H1), *Cooperia* (H2), *Trichostrongylus* (H3), *Oesophagostomum* (H4), and *Trichuris* (H5)) were collected from each group and counted. The number of each species of helminthes and the arithmetic averages are shown in Table 3. The group of cattle treated with the composition of the present invention (Example 1) had the lowest number of helminthes recorded for each of the species, except for *Trichostrongylus*, in which case the comparative formula was as efficacious. Overall, the total number of worms (all species) for the composition of the present invention was less than half of the comparative composition.

TABLE 3

Effect of high-dose doramectin compositions against different species of helminths in cattle-arithmetic average

| Group | H1 | H2 | H3 | H4 | H5 | Total |
|---|---|---|---|---|---|---|
| | Helminth Species | | | | | |
| Control | 9759 | 1880 | 28 | 2305 | 5 | 13977 |
| | 760 | 13608 | 0 | 525 | 5 | 14898 |
| | 9332 | 2523 | 178 | 2080 | 0 | 14113 |
| | 4951 | 10 | 57 | 725 | 0 | 5743 |
| | 2756 | 2910 | 195 | 1285 | 0 | 7146 |
| | 2833 | 446 | 224 | 420 | 60 | 3983 |
| | 4326 | 336 | 51 | 85 | 10 | 4808 |
| | 2496 | 1305 | 0 | 70 | 1 | 3872 |
| Total | 37213 | 23018 | 733 | 7495 | 81 | 68540 |
| Average | 4651.63 | 2877.25 | 91.63 | 936.88 | 10.13 | 8567.50 |
| Comparative Composition Example 2 | 4024 | 360 | 0 | 50 | 0 | 4434 |
| | 1072 | 7400 | 0 | 240 | 10 | 8722 |
| | 103 | 460 | 0 | 10 | 10 | 583 |
| | 6076 | 3510 | 0 | 10 | 260 | 9856 |
| | 2412 | 7160 | 0 | 150 | 40 | 9762 |
| | 1478 | 1050 | 0 | 20 | 10 | 2558 |
| | 1530 | 2110 | 0 | 40 | 0 | 3680 |
| | 410 | 430 | 0 | 400 | 10 | 1250 |
| Total | 17105 | 22480 | 0 | 920 | 340 | 40845 |
| Average | 2138.13 | 2810.00 | 0.00 | 115.00 | 42.50 | 5105.63 |
| Composition Example 1 | 2766 | 400 | 0 | 110 | 0 | 3276 |
| | 1160 | 10 | 0 | 0 | 0 | 1170 |
| | 1098 | 2361 | 0 | 70 | 10 | 3539 |
| | 1301 | 1170 | 0 | 120 | 0 | 2591 |
| | 484 | 40 | 0 | 0 | 0 | 524 |
| | 3920 | 10 | 0 | 90 | 0 | 4020 |
| | 218 | 40 | 0 | 0 | 0 | 258 |
| | 169 | 1370 | 0 | 20 | 0 | 1559 |
| Total | 11116 | 5401 | 0 | 410 | 10 | 16937 |
| Average | 1389.50 | 675.13 | 0.00 | 51.25 | 1.25 | 2117.13 |

Study 3

The veterinary composition of the instant invention (Example 1) was compared against commercial high-dose products to assess efficacy against cattle grub (*Dermatobia hominis* larvae) infestations. Three high-dose avermectin compositions were assessed. Forty cattle were selected based on visual inspection of larval infestation. The animals were randomly assigned to treatment groups based on the mean of two pre-treatment counts (Days −2 and −1) of *D. hominis* larvae. Four groups of 10 animals each were formed as follows: T01 was a control (saline), T02 received Doramectin 3.5% (Example 1), T03 received Ivermectin 3.15% (Ivomec Gold, Merial), and T04 received Ivermectin 4.0% (Master LP, Ouro Fino). Animals were maintained within the same pasture boundary in Brazil for the duration of the study. Water and mineral supplement was provided ad libitum. Cattle were dosed subcutaneously at 1 mL/50 Kg dose on Day 0. Larval nodules were counted on Days −2, −1, 3, 7, 14, and weekly thereafter until 133 days post-treatment. Results are shown in FIG. 1. Doramectin 3.5% showed superior therapeutic and persistent efficacy against *D.hominis* larvae as compared to the other high-dose commercial ivermectin compositions. Efficacy (geometric means) higher than 90% was attained from 14 to 105 days, 28 to 77 days, and 28 to 84 days post treatment for the Doramectin 3.5%, Ivermectin 3.15% and Ivermectin 4.0% doses, respectively.

Study 4

Comparatively, withhold times for commercial low-dose doramectin, high-dose ivermectins, and a high-dose combination containing ivermectin and abamectin were assessed against high-dose doramectin (Example 1). The withhold times are based upon residual drug concentrations obtained from animal tissue (skeletal meat, fat, kidney, and liver) as reported by each company in their respective product labels as registered with the Brazilian Ministry of Agriculture (MAPA). Product labels report withhold time in days and months. For consistency, withhold time is represented in days, where 1-month is 30-days. Withhold times are shown in Table 4. The high-dose doramectin composition provides a withhold time that is one-half the time for the other high-dose compounds. Therefore, cattle can be slaughtered for meat consumption sooner following treatment with high-dose doramectin than can be achieved from the other high-dose avermectins.

6. The composition of claim 5, wherein the benzyl alcohol is 6% and the tocopherol is 0.05% tocopherol acetate.

7. The composition of claim 1, wherein the doramectin is 3.5% w/v, the cotton seed oil is 55% v/v, the benzyl benzoate is 39% v/v, further comprising an auxiliary excipient and a preservative, wherein the auxiliary excipient is 6% benzyl alcohol, and the preservative is 0.05% tocopherol acetate.

8. The composition of claim 7, further comprising at least one fat soluble vitamin selected from Vitamin A, Vitamin D, and Vitamin E.

9. A method for the treatment or control of parasites in an animal comprising administering to said animal an effective amount of an antiparasitic composition comprising (a) 3-6% w/v doramectin, (b) 39-60% v/v cottonseed oil; (c) 30-50% benzyl benzoate; and optionally d) one or more each of a preservative, auxiliary excipient, and fat soluble vitamin.

10. The method of claim 9, wherein the doramectin is 3.5% w/v, the cotton seed oil is 55% v/v, the benzyl benzoate is 39% v/v, the auxiliary excipient is benzyl alcohol, and the preservative is tocopherol.

11. The method of claim 10, wherein the benzyl alcohol is 6% and the preservative is 0.05% tocopherol acetate.

12. The method of claim 9, wherein the composition is parenterally administered to the animal.

13. The method of claim 12, wherein said parenteral administration is subcutaneous.

14. The method of claim 13, wherein said animal is livestock.

15. The method of claim 14, wherein livestock is cattle.

16. A veterinary combination antiparasitic composition comprising (a) 1-3% w/v doramectin, (b) 1-3% w/v of one or

TABLE 4

Reported withhold times for beef cattle relative to residual concentrations of avermectins in meat

| Product | Manufacturer | Avermectin concentration | Dose (mg/kg) | Withhold Time (days) | MAPA Registration # (year) |
|---|---|---|---|---|---|
| Dectomax | Pfizer | 1.0% doramectin | 0.20 | 35 | 4.055 (1992) |
| Composition Example 1 | Pfizer | 3.5% doramectin | 0.70 | 63 | — |
| Ivomec Gold | Merial | 3.15% ivermectin | 0.63 | 122 | 6.103 (1997) |
| Solution 3.5% LA | Intervet - Schering-Plough | 2.25% ivermectin + 1.25% abamectin | 0.70 (0.45 + 0.25) | 122 | 8.691 (2003) |
| Megamectin 3.5 | Novartis | 3.5% ivermectin | 0.70 | 120 | 8.632 (2003) |
| Master LP | Ouro Fino | 4.0% ivermectin | 0.80 | 130 | 9.208 (2006) |

What is claimed is:

1. A veterinary antiparasitic composition comprising (a) 3-6% w/v doramectin, (b) 39-60% v/v cottonseed oil, (c) 30-50% v/v benzyl benzoate; and optionally d) one or more each of a preservative, auxiliary excipient, and fat soluble vitamin.

2. The composition of claim 1, further comprising one or more preservatives.

3. The composition of claim 2, further comprising one or more auxiliary excipients.

4. The composition of claim 3, further comprising one or more fat soluble vitamins selected from the group consisting of Vitamin A, Vitamin D, and Vitamin E.

5. The composition of claim 3, wherein the doramectin is 3.5% w/v, the cotton seed oil is 55% v/v, the benzyl benzoate is 39% v/v, the auxiliary excipient is benzyl alcohol, and the preservative is tocopherol.

1-3% combined w/v of more than one antiparasitic agent selected from the group consisting of abamectin, ivermectin, eprinomectin, moxidectin, and milbemycin; (c) 39-75% v/v cottonseed oil, (d) 25-50% v/v benzyl benzoate; and optionally (e) one or more each of a preservative, auxiliary excipient, and fat soluble vitamin, wherein said vitamin is selected from the group consisting of Vitamin A, Vitamin D, and Vitamin E.

17. The composition of claim 16 further comprising one or more preservatives and one or more auxiliary excipients.

18. The composition of claim 17, further comprising one or more fat soluble vitamins selected from the group consisting of Vitamin A, Vitamin D, and Vitamin E.

19. A method for the treatment or control of parasites in an animal comprising administering to said animal an effective amount of a composition comprising (a) 1-3% w/v doramectin, (b) 1-3% w/v of one or 1-3% combined w/v of more than one antiparasitic agent selected from the group consisting of abamectin, ivermectin, eprinomectin, moxidectin, and milbemycin; (c) 39-75% v/v cottonseed oil, (d) 25-50% v/v benzyl benzoate; and optionally e) one or more each of a preservative, auxiliary excipient, and fat soluble vitamin, wherein said vitamin is selected from the group consisting of Vitamin A, Vitamin D, and Vitamin E.

20. The method of claim 19, further comprising at least one preservative and at least one auxiliary excipient and wherein animal is livestock.

* * * * *